United States Patent [19]

Straw

[11] Patent Number: 4,808,630

[45] Date of Patent: Feb. 28, 1989

[54] METHOD OF TREATING PSYCHOTIC ILLNESSES

[75] Inventor: Gregory M. Straw, Fairfax, Va.

[73] Assignee: United States of America, Washington, D.C.

[21] Appl. No.: 158,035

[22] Filed: Feb. 16, 1988

Related U.S. Application Data

[63] Continuation of Ser. No. 4,008, Jan. 16, 1987, abandoned.

[51] Int. Cl.$^4$ ............................................ A61K 31/445
[52] U.S. Cl. .................................................... 514/317
[58] Field of Search ......................................... 514/317

[56] References Cited

U.S. PATENT DOCUMENTS

| | | | |
|---|---|---|---|
| 4,200,647 | 4/1980 | Bollag et al. | 424/305 |
| 4,371,673 | 2/1983 | Pitha | 525/426 |
| 4,642,318 | 2/1987 | Wolff | 514/560 |

OTHER PUBLICATIONS

Grace et al., Neuroscience, vol. 10, No. 2, pp. 333–348 (1983).
Hazen et al., Journal. Amer. Assoc. Dermat. pp. 278–279, vol. 9, No. 2 (1983).
Leitna et al., Brit. J. Nutr. (1984), 18, 115–127.
Pitts et al., Carcenogenesis, vol. 7, No. 6, pp. 1003–1110, (1986).
Studt et al., Z. Hautkr 61, Heft 10 (1986), pp. 743–754.

*Primary Examiner*—Stanley J. Friedman
*Attorney, Agent, or Firm*—Jon S. Saxe; Bernard S. Leon; A. Kate Huffman

[57] ABSTRACT

This invention is directed towards methods for treating patients having a psychotic illness such as schizophrenia and/or inhibiting the occurrence of movement disorders in patients receiving or having received a neuroleptic medication by administering to the patients a pharmaceutically effective amount of a retinoid, such as retinoic acid, and particularly isotretinoin.

17 Claims, No Drawings

METHOD OF TREATING PSYCHOTIC ILLNESSES

This application is a continuation, of application Ser. No. 004,008, filed Jan. 16, 1987, now abandoned.

FIELD OF THE INVENTION

The invention relates to the treatment of pyschotic illness, particularly schizophrenia, using therapeutic compositions which comprise retinoids, including the retinoic acids, particularly retinoic acid isomers such as 13-cis-retinoic acid and 13-trans-retinoic acid.

BACKGROUND OF THE INVENTION

Psychotic disorders involve an impairment of mental functioning to the extent that it interferes grossly with an individual's ability to meet the ordinary demands of life, characterized generally by severe affective disturbance, profound introspection, and withdrawal from reality with failure to test and evaluate external reality adequately formation of delusions or hallucinations, and regression presenting the appearance of personality disintegration. Included in this grouping are the affective disorders, paranoid states and schizophrenias.

Psychotic disorders may be treated in some cases by the administration of a major tranquilizer, or neuroleptic such as 4-[4-(p-chlorophenyl)-4-hydroxypiperidino]-4′-fluorobutyrophenone (hereinafter "haloperidol" or "HAL"). The precise mechanism of action of haloperidol has not been clearly established.

Haloperidol generally reaches a steady state blood level after approximately five days of daily dosage and intra-individual variation in blood concentration is limited. Large individual differences in such variables as absorption, distribution, metabolism and excretion, however, result in great inter-individual differences in concentrations at the same dose. These variables are known to be affected by concomitant administration of other drugs. Commonly used drugs that may affect neuroleptic blood concentrations include lithium, trihexyphenidyl, anticonvulsants, tricyclic and monoamine oxidase inhibitor antidepressants, oral contraceptives, and antacids.

The most often reported effect is for HAL concentrations to decrease with concurrent administration of anticonvulsant drugs such as carbamazepine or phenobarbitol. The exact mechanisms for this effect are not known, but the induction of metabolic enzymes may be the common pathway. A primary metabolite of HAL in humans is the reduced form, 4-(4-(4-chlorophenyl)-4-hydroxy-piperdinyl)-1-(4-fluorophenyl)-1-butanol, hereinafter hydroxy-haloperidol (OH-HAL). However, the actual mechanism for its production in vivo has not been proven. Other possibilities are that the drugs affect the absorption, distribution, metabolism or excretion of haloperidol.

The behavioral and physiological effects of haloperidol and other neuroleptics have been thought to be altered by the concurrent administration of a number of medications above and beyond any effect on blood concentrations. The primary example of this is lithium and the controversy that began with a report that a deleterious synergism may occur. Also, it has been reported that in the rat a synergism may occur between the haloperidol and ascorbic acid.

Retinoic acids, particularly the isomers isotretinoin (13-cis-retinoic acid) and tretinoin (13-trans-retinoic acid) are endogenously occurring acid metabolites of vitamin A that are also used clinically for the treatment of some skin diseases and experimentally for some cancers. Retinoic acids have been shown to induce changes in many cellular and extracellular components, and can partially replace vitamin A in some critical activities for growth and development. However, there have been no drug interactions reported for retinoic acids previously.

Isotretinoin is currently used for the oral treatment of cystic acne with a dose in the range of 1 to 2 mg/kg/day in two divided daily doses.

Basic science studies have noted that the retinoic acids may regulate the function of protein kinase C in a complex fashion. This kinase, in turn, has been demonstrated in high concentrations in the brain in specific areas including the pathways involved in dopaminergic activity (Worley, P. F., Baraban, J. M., Snyder, S. H., Heterogenous localization of protein kinase C in rat brain: autoradiographic analysis of phorbol ester receptor binding. J. Neuroscience, 1986, 6(1), 199–207). Biochemically, protein kinase C is integral to some second messenger systems mediating neuronal activity. In this fashion, retinoids may have an effect on specific brain activity including dopaminergic transmission and its putative roles in motor activity and psychotic illness (Meltzer, H. Y., Goode, D. J., Fang, V. S., et al. Dopamine and schizophrenia. Lancet, 1976, 2, 1142). It has been postulated, for instance, that abnormalities of this kinase-mediated second messenger function in dopaminergic response may be related to the pathophysiology of dyskinesias (Poiletman, R., and Goldschmidt, T. Treatments of tardive dyskinesia as viewed from a calcium ion perspective. The Psychiatric Forum Spring: 1–5, 1984).

Complex pharmacokinetic interactions of psychoactive drugs are known to occur (Gaultieri, C. T. and S. F. Powell: Psychoactive drug interactions. J. Clin. Psychiat., 1978, 39, 720–729). However it is not known in the prior art of any interactions of psychoactive medications with any retinoids.

SUMMARY OF THE INVENTION

In accordance with the present invention it has been discovered that there is a pharmacokinetic interaction between haloperidol and retinoids, including retinoic acid, which results in decreased serum levels of haloperidol in a patient with little or no loss of efficacy for the treatment of psychotic illness. Additionally, it has been discovered that the retinoids themselves have a direct psychotropic effect.

Therefore, the present invention relates to a method of treating a patient having a psychotic illness, such as schizophrenia, by the systemic administration of a retinoid to the patient in a pharmaceutically effective amount for treating the psychotic illness. The invention also relates to a method for inhibiting the occurrence of movement disorders, such as tardive dyskinesia and extra-pyramidal side effects resulting from treatment with a neuroleptic such as haloperidol, which method comprises the concurrent administration of a retinoid in a pharmaceutically effective amount for inhibiting the occurrence of the movement disorders.

DESCRIPTION OF THE PREFERRED EMBODIMENT

Retinoids reduce serum levels of neuroleptic medication in patients to whom the retinoids are administered. Moreover, in some patients, the administration of retinoids may, themselves relieve some of the symptoms of psychotic illnesses such as schizophrenia.

One advantage of administering retinoids to a patient afflicted with psychotic illness is that it relieves the patient's symptoms without the dyskinesias or parkinsonium that are associated the the neuroleptic medications such as haloperidol. Moreover, when retinoids are administered to patients who are also receiving one of the commonly administered antipsychotic drugs, such as haloperidol, the retinoids ameliorate the dyskinesias and parkinsonium symptoms which might otherwise result from treatment with the antipsychotic.

In accordance with this invention, a pharmaceutical composition comprising an amount of a retinoid which is effective in the treatment of a psychotic illness, such as schizophrenia and a medicinally inert pharmaceutically acceptable carrier material is administered to a human suffering from the psychotic illness.

As used herein, "retinoid" denotes the known vitamin A compounds in naturally occuring forms such as retinol, retinal, retinyl esters, retinoic acid as well as the known synthetic analogs of vitamin A. The ring on the analogs may be aromatic or heteroaromatic and the side chain may be optionally substituted with a halide such as chloride. The terminal group may be oxidized, reduced, esterified, etc. The alkali metal (sodium potassium, etc.) and alkaline earth metal (magnesium, calcium, etc.) salts of a retinoic (also called "retinoid carboxylic") acid are also included herein.

Preferred retinoids for practicing the present invention are the various geometric isomers (cis/trans) of retinoic acid, including the alkali metal and alkaline earth metal salts thereof as well as their esters having lower alkyl groups of 1 to 6 carbon atoms.

Particularly preferred retinoic acids for the treatment of psychotic illnesses such as schizophrenia are 13-cis-retinoic acid (isotretinoin) and 13-trans-retinoic acid (tretinoin).

In accordance with this invention the retinoids can be administered in a pharmaceutically acceptable dosage form in either a parenteral or enteral mode preferably orally. These pharmaceutical compositions of the invention contain the retinoids as an active ingredient in association with a compatible pharmaceutically acceptable carrier material. Any conventional carrier material can be utilized. The carrier material can be an organic or inorganic inert carrier material suitable for enteral, percutaneous or parenteral administration. Suitable carriers include water, gelatin, gum arabic, lactose, starch, magnesium stearate, talc, vegetable oils, polyalkyleneglycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: (a) a solid form for oral administration such as tablets, capsules, pills, dragees, powders, granules, and the like; (b) a liquid form for oral administration such as solutions, syrups, suspensions, elixirs and the like; and (c) preparations for parenteral administration such as sterile solutions, suspensions or emulsions. The pharmaceutical preparations may be sterilized and/or may contain adjuvants such as preservatives, stabilizers, wetting agents, emulsifiers, salts for varying the osmotic pressure and/or buffers.

Parenteral dosage forms may be infusions or injectable solutions which can be injected intravenously or intramuscularly. These preparations can also contain other medicinally active substances. For parenteral formulations a daily dosage of from about 0.01 mg to about 3 mg per Kg of body weight, preferably from about 0.05 mg to about 1 mg per Kg of body weight of the patient most preferably about 0.5 mg per kg of body weight of the patient will be utilized. Additional additives such as flavoring agents, preservatives, stabilizers, emulsifying agents, buffers and the like may be added in accordance with accepted practices of pharmaceutical compounding.

A preferred oral dosage form comprises capsules of hard or soft gelatin methylcellulose or of another suitable material easily dissolved in the digestive tract. The enteral dosages contemplated in accordance with the present invention will vary in accordance with the needs of the individual patient as determined by the prescribing physician. Generally, however, a daily dosage of from about 0.01 mg to about 3 mg per Kg of body weight, preferably from about 0.05 mg to about 1 mg per Kg of body weight of the patient and most preferably about 0.5 mg per Kg of body weight of the patient is utilized. This dosage may be administered according to any dosage schedule determined by the physician in accordance with the requirements of the patient.

It is likewise within the purview of the present invention to incorporate a retinoid in any desired amount for enteral administration within the oral unit dosage form. It is preferred, however, to formulate preparations containing the active retinoid in such a manner that each dose contains from about 0.05 mg to about 100 mg, particularly from about 5 mg to about 40 mg of the active substance with suitable therapeutically inert fillers and diluents. It is especially preferred to incorporate such a dosage into gelatin capsules and tablets.

Gelatin capsules containing either 10 mg, 20 mg or 40 mg of isotretinoin are available from Hoffman-La Roche Inc., Nutley, N.J.

In accordance with this invention, therefore, isotretinoin and tretinoin as well as the other retinoids which show a pronounced anti-psychotic activity, can thus be used in the pharmaceutical preparations mentioned above, for reducing psychotic symptoms, in particular, and for the treatment of schizophrenia. Also, these pharmaceutical preparations can be used to inhibit the occurence of movement disorders, particularly tardive dyskinesia and extra-pyramidal side effects of a concurrently administered neuroleptic such as haloperidol.

The dosage for treatment typically depends on the route of administration, the age, weight and condition of the individual.

The following examples illustrate the invention. Examples 1-5 are directed to the preparation of gelatin capsule pharmaceutical preparations containing isotretinoin for oral administration.

EXAMPLE 1

| 25% Isotretinoin Suspension | | |
|---|---|---|
| Item | Ingredient | grams/Kg |
| 1 | Isotretinoin | 250.00 |
| 2. | Purified Beeswax | 36.38 |
| 3. | Hydrogenated Soybean Oil Flakes | 36.38 |
|  | Hydrogenated Vegetable Oil | 145.73 |
| 4. | Soybean Oil, USP | 528.61 |

-continued

| | 25% Isotretinoin Suspension | |
|---|---|---|
| Item | Ingredient | grams/Kg |
| 5. | Butylated Hydroxyanisole | 0.50 |
| 6. | Disodium Edetate | 2.40 |

Ingredient items 2 through 4 were melted at about 70° C. using a suitable heater and mixed using a suitable mixer.

Next, ingredient item 5 was heated to about 38° C. using a suitable heater and ingredient item 6 was incorporated and dissolved into ingredient item 5 while mixing with a suitable mixer and maintaining the temperature at about 38° C.

Ingredient items 2 through 6 were then combined while being mixed and were then cooled to about 40° C. following mixing.

Isotretinoin was then added with mixing followed by the addition of ingredient item 7 while mixing.

The resulting mixture was cooled to room temperature, this forming the 25% isotretinoin suspension.

In the following examples, the term "wax mixture" shall refer to a mixture of 1 part by weight purified beeswax, 1 part by weight hydrogenated soybean oil flakes and 4 parts by weight hydrogenated vegetable oil.

EXAMPLE 2

| Gelatin Capsule for Oral Administration - 5 mg | |
|---|---|
| 25% Isotretinoin Suspension (Example 1) | 21 mg |
| Butylated hydroxyanisole | 0.097 mg |
| Disodium edetate | 0.463 mg |
| Wax mixture | 42.5 mg |
| Soybean oil | 100.94 mg |

The above ingredients were melted and mixed and filled into gelatin push-fit capules of size No. 3.

EXAMPLE 3

| Gelatin Capsule for Oral Administration - 10 mg | |
|---|---|
| 25% Isotretinoin suspension (Example 1) | 42 mg |
| Butylated hydroxyanisole | 0.08 mg |
| Disodium edetate | 0.40 mg |
| Wax mixture | 36.30 mg |
| Soybean oil | 86.22 mg |

The above ingredients were melted and mixed and filled into gelatin push-fit capsules of size No. 3.

EXAMPLE 4

| Gelatin Capsule for Oral Administration - 20 mg | |
|---|---|
| 25% Isotretinoin suspension (Example 1) | 84 mg |
| Butylated hydroxyanisole | 0.166 mg |
| Disodium edetate | 0.792 mg |
| Wax mixture | 72.6 mg |
| Soybean oil | 172.442 mg |

The above ingredients were melted and mixed and filled into gelatin push-fit capsules of size No. 6.

EXAMPLE 5

| Gelatin Capsule for Oral Administration - 40 mg | |
|---|---|
| 25% Isotretinoin suspension (Example 1) | 108 mg |
| Butylated hydroxyanisole | 0.1 mg |
| Disodium edetate | 0.6 mg |
| Wax mixture | 44 mg |
| Soybean oil | 117.3 mg |

The above ingredients were melted and mixed and filled into gelatin push-fit capsules of size No. 6.

The retinoids, especially retinoic acid isomers, alone or in combination with another neuroleptic, are effective neuroleptics in humans in the treatment of human psychotic illness, including schizophrenia, and in producing tranquilization. The retinoids, especially retinoic acid isomers are also effective in altering the tissue and serum concentration of concurrently administered neuroleptics such as haloperidol in humans. These effects are demonstrated in the following examples.

The following examples 6–7 show a pharmacokinetic interaction between haloperidol and retinoic acid in humans. In particular, Example 7 also reveals a direct psychotropic effect of retinoic acid.

EXAMPLE 6

A 22 year old male patient (subject 1) was diagnosed as having schizophrenia and was receiving haloperidol at a dose of 0.2 mg/Kg/day in two divided daily doses. His blood level of haloperidol at that time and dose was 13.7 ng/ml (mean of three samples). He was begun subsequently on a concurrent course of isotretinoin at a once daily dose of 0.6 mg/Kg/day orally for the treatment of cystic acne. There was a decrease in the haloperidol blood level following initiation of the isotretinoin to 8.8 ng/ml (1 sample). There was no adverse change in his clinical condition after starting isotretinoin despite the reduction in haloperidol blood levels.

EXAMPLE 7

A 29 year old male patient (subject 2) diagnosed as having schizophrenia was initially maintained in double blind placebo fashion on haloperidol and benztropine for over ten weeks with complaints of persistent auditory hallucinations and poor concentration. His affect was blunted, and he was socially withdrawn. Laboratory evaluation, physical exam, CT head scan, EEG, and EKG were within normal limits.

After his behavioral status as measured by the Brief Psychiatric Rating Scale (BPRS) has stabilized, he was placed on coded active haloperidol at 30 mg/day (0.4 mg/Kg/day). The BPRS was performed by nursing staff blind to the haloperidol and benztropine status. He developed parkinsonian symptoms and was placed on benztropine at 4 mg/day increased to 8 mg/day. He clinically improved after being changed from placebo to active haloperidol as reflected by a decrease in his BPRS items. The positive symptoms scale of the BPRS (here called PosBPRS and including hallucinations, delusions, and disorganized thinking) average over the seven days prior to each medication change was 1.83 in his first drug free period, falling over four weeks on haloperidol to 1.00. His serum haloperidol level as measured by high performance liquid chromatography was 19.1 ng/ml. At that time he requested that the dermatologist put him on isotretinoin for his cystic acne because his sibling has recently had a good response. When on isotretinoin he received 40 mg in a single daily dose (0.5 mg/Kg/day). A further improvement in his clinical presentation and PosBPRS (0.066) was then seen in spite of a drop over the next 6 weeks of the serum haloperidol blood levels to near zero (<1 ng/ml or unmeasurable on our assay). The serum haloperidol concentration was unmeasurable on four successive samples over the next six weeks in spite of an increase of the haloperidol dose to 60 mg/day (0.8 mg/Kg/day). This increase in dose was also followed by a slight further decrease in his PosBPRS scores (0.55).

The isotretinoin then was stopped. Within 2 days the patient became more parkinsonian and more irritable, and began to present ideas of reference and complaints of poorly defined "disturbing thoughts". Two days after stopping isotretinoin his serum haloperidol had risen to 10 ng/ml. The haloperidol, benztropine, and isotretinoin then were discontinued. The haloperidol levels fell to zero within one week. His PosBPRS scores rose to 1.12 over the next three weeks.

The isotretinoin was then restarted without other medications and his PosBPRS scores fell slowly over a six week period to 0.35. The isotretinoin was again stopped. After the isotretinoin was discontinued his clinical presentation worsened with flattening of affect, loss of motivation, and increasing social withdrawal. The deterioration was clinically noticable by three days after withdrawal of the isotretinoin, and his PosBPRS increased to 2.37 after 5 weeks drug free.

Neuropsychological evaluation during the second period of isotretinoin treatment reflected no significant changes in performance levels compared to the mostly above average functioning at the end of the preceding three week drug free period. Exceptions were verbal fluency (improved) and block design (declined). In contrast, neuropsychological performance 5 weeks after the second isotretinoin course was discontinued showed dramatic declines to below pretreatment levels on measures of simple and complex memory, verbal fluency, attention and cognitive efficiency.

The effect of isotretinoin on haloperidol blood levels is illustrated in Table 1.

TABLE 1

EFFECT OF ISOTRETINOIN ON HALOPERIDOL BLOOD LEVELS IN TWO SUBJECTS

| SUBJECT | DATE | HALOPERIDOL SERUM CONCENTRATIONS | HALOPERIDOL DOSE (MG/DAY) | ISOTRETINOIN DOSE (MG/DAY) | PosBPRS 7 DAY AVE (MG/DAY) |
|---|---|---|---|---|---|
| 1 | 8/13/85 | 13.7 | 14 | 0 | |
| 1 | 12/3/85 | 14.9 | 14 | 0 | |
| 1 | 12/11/85 | 11.6 | 14 | 0 | |
| 1 | 12/17/85 | 10.7 | 14 | 40 | |
| 1 | 12/17/85 | 7.0 | 14 | 40 | |
| 2 | 7/30/85 | 0.0 | 0 | 0 | 1.83 |
| 2 | 8/14/85 | 17.6 | 30 | 0 | |
| 2 | 8/27/85 | 19.1 | 30 | 0 | 1.00 |
| 2 | 9/10/85 | 5.4 | 30 | 40 | |
| 2 | 9/17/85 | 8.6 | 30 | 40 | |
| 2 | 9/23/85 | 3.5 | 30 | 40 | 0.66 |
| 2 | 10/14/85 | <1.0 | 60 | 40 | |
| 2 | 10/21/85 | <1.0 | 60 | 40 | |
| 2 | 11/6/85 | <1.0 | 60 | 40 | 0.55 |
| 2 | 11/19/85 | | | DISC | |
| 2 | 11/22/85 | <1.0 | 60 | 0 | |
| 2 | 11/25/85 | 10.0 | 60 | 0 | |
| 2 | 11/26/85 | | DISC | 0 | |
| 2 | 12/3/85 | <1.0 | 0 | 0 | |
| 2 | 12/9/85 | | | 0 | 1.12 |
| 2 | 12/10/85 | | | 40 | |
| 2 | 2/8/86 | | 0 | 40 | 0.35 |
| 2 | 2/11/86 | | | 0 | |
| 2 | 3/14/86 | | | 9 | 1.57 |

The following examples show animal test data for isotretinoin (Examples 8–9) as well as tretinoin (Example 9).

EXAMPLE 8

Female Sprague-Dawley rats were obtained from Zivic-Miller Laboratories and weighed 380 g ($\pm$s.d.10) when tested.

The HAL and OH-HAL concentrations were measured electrochemically after high performance liquid chromatography (HPLC) in accordance with the method of Korpi et al. (Korpi, E. R., B. H. Phelps, H. Granger, W. Chang, M. Linnoila, J. L. Meek & R. J. Wyatt: Simultaneous determination of haloperidol and its related metabolite in serum and plasma by isocratic liquid chromatography with electrochemical detection. Clin. Chem., 1983, 29, 624–628). Concentrations were reported in nanograms per milliliter (ng/ml) of spun serum, red blood cells, or homogenized brain tissue. The volumes of the brain samples were calculated from the wet weight of the frozen tissue using the specific gravity measured in control animals at 0.95 g/ml. Overall significance of the effect of isotretinoin ("ISOT") was determined by a repeated measures MANOVA F test with two within-subject variables: tissue compartment and test performed. Significance of the difference between means was then determined at $p < 0.05$ by the method of Tukey for unbalanced data.

All rats received HAL 1 mg/kg (in 1% lactic acid in physiologic saline injected in a volume of 1 ml/kg) subcutaneously. ISOT was injected intraperitoneally in neat DMSO (at 1 mg/kg) at concentrations to obtain the required dose in mg/kg. DMSO was used to assure complete mobilization of the ISOT in the liquid phase. All ISOT solutions were prepared fresh for each injection series. All work with the ISOT including the injections was done under amber light to avoid photodecomposition of the ISOT.

The animals were marked for identification and the injections were given sequentially at one per month at each session so that each animal received the haloperidol first, followed by the isotretinoin 36 minutes later. There were 35 animals divided into four groups by isotretinoin dose: 0 mg/kg (N=11), 1 mg/kg (N=8), 5 mg/kg (N=8), 10 mg/kg (N=8). The five injection sessions were done over 3 days beginning at 9 am, 4 pm, 9 am, 4 pm, and 9 am, with the animals then sacrificed by decapitation starting at 1 pm of the third day at one per minute in the same order in which they were injected. Core blood was collected, cooled on ice, spun for 20 minutes at 1000 g, and the serum and red cells separated and frozen in plastic tubes at $-40$ C. until assayed. Within one minute after sacrifice the brain was removed and separated from the brain stem above the pons and placed on ice for approximately 30 minutes. The cerebrum and rostral brain stem were divided in half between the hemispheres and stored at $-40$ C. One hemisphere and attached rostral brain stem from each animal were weighed, homogenized in double distilled water and an aliquot removed and alkalinized for extraction prior to assay by HPLC.

The concentrations of HAL and OH-HAL were reported in Table 2 for the three tissue compartments: serum, red blood cells and brain. To examine the effect of ISOT on the metabolite/drug relationship, the ratio of OH-HAL to HAL in each compartment was also presented. Thus, there were three tissue compartments each with three test measures evaluated in each animal.

TABLE 2**

| | ISOTRETINOIN (mg/kg) | | | |
|---|---|---|---|---|
| | 0 | 1 | 5 | 10 |
| Serum Haloperidol | 44.8 ± 7.1 | 67.5 ± 8.0 | 73.3 ± 17.1 | 97.5 ± 19.0* |
| Serum Oh-haloperido | 1.8 ± .2 | 4.2 ± .5* | 3.3 ± .2* | 3.0 ± .4 |
| Serum ratio (oh-h/hal) | 0.038 | 0.060 | 0.044 | 0.029 |
| RBC Haloperidol | 13.4 ± 2.4 | 18.1 ± 4.8 | 33.8 ± 16.8 | 37.2 ± 8.8 |
| RBC Oh-haloperidol | <2 | <2 | <2 | 3.2 ± .8* |
| RBC ratio (oh-h/hal) | <.15 | <.11* | <.06* | 0.09 |
| Brain Haloperidol | 465 ± 44 | 413 ± 31 | 344 ± 26 | 739 ± 90* |
| Brain Oh-haloperidol | 96 ± 13 | 64 ± 8 | 45 ± 4 | 152 ± 28 |
| Brain ratio (oh-h/hal) | 0.216 | 0.15 | 0.13* | 0.19 |

**Table 2. Summarized data for each compartment (mean ± standard error) in nanograms/milliliter (ng/ml).
*denotes significant difference from controls at the $p < .05$ level by Tukey's method for multiple comparisons of the means.

The overall between-subject effects of ISOT dose were significant with $F(3,31)=10.06$, $p=0.0473$. Within-subject effects for tissue compartment and test were both significant with $F(3,62)=245.41$, $p=0.0001$ and $F(3,62)=396.95$, $p=0.0001$, respectively. Significant interaction effects were also seen between ISOT dose and both the compartment and the test type with $F(6,62)=8.95$, $p=0.0001$ and $F(6,62)=9.75$, $p=75$, $p=0.0001$, respectively.

Serum HAL concentrations were affected significantly with $F(3,31)=2.96$, $p=0.0473$. The means for serum HAL tended to increase with each increase in ISOT dose, becoming significantly ($p<0.05$) different from controls at the 10 mg/kg level. Red blood cell concentrations of HAL were not significantly altered overall with $F(3,31)=1.71$, $p=0.186$. Brain HAL was significantly altered overall with $F(3,31)=9.75$, $p=0.0001$. While the brain mean HAL concentration tended to decrease at the intermediate doses, it was significantly increased ($p<0.05$) at the 10 mg/kg dose.

The serum OH-HAL concentrations were altered significantly with $F(3,31)=9.56$, $p=0.0001$. The means of the serum OH-HAL were significantly increased over controls ($p<0.05$) at the 1 and 5 mg/kg doses of ISOT. Many of the measured OH-HAL values in the red blood cells, particularly at the 1 and 5 mg/kg doses of ISOT, were at or below the minimum sensitivity of the assay reported as <2 ng/ml by Korpi et al. (13). For statistical purposes these values were treated as representing primarily the baseline variance of the assay. However, the values were reported here only as their upper limit, <2 ng/kg. By this procedure, red blood cell OH-HAL concentrations were significantly altered overall on the repeated measured MANOVA, $F(3,31)=11.1$, $p=0.001$. The mean of the red blood cell OH-HAL concentration at the 10 mg/kg ISOT dose was disignificantly ($p<0.05$) elevated above baseline. Brain OH-HAL values were also significantly altered overall, $F(3,31)=8.27$, $p=0.0003$, and the individual means tended to follow the pattern of the red cells with a decrease at the low and an increase at the higher dose. However, no individual mean of the brain OH-HAL reached significance.

The ratios of serum OH-HAL to HAL were significantly altered by isotretinoin, $F(3,31)=3.38$, $p=0.0306$. However, no mean at any given dose differed significantly from controls. Again for the red blood cell values, the ratios representing the very low values are considered to represent the baseline variance of the measures, and the reported values are truncated at their calculated upper limit. Following this procedure, the ratio in the red blood cells was significantly altered overall, $F(3,31)=12.66$, $p=0.0001$, and the separate means were significantly lowered ($p<0.05$) at the intermediate doses. The brain ratio of OH-HAL to HAL was significantly changed by ISOT as well, $F(3,31)=4.86$ at prob>F=0.0069, with only the mean at the 5 mg/kg dose decreasing enough to reach significance ($p<0.05$).

Based upon the above data, ISOT when given in DMSO to rats increases the concentrations of HAL and OH-HAL in the serum, brain, and red blood cells. Moreover, there is the appearance at the intermediate ISOT of a decrease in the brain concentrations of both HAL and OH-HAL. This tendency toward a biphasic dose dependent effect of ISOT in the brain and red cells is supported by the finding of a similarly biphasic and significant ($p<0.05$) dose dependency in the ratios in these two compartments. Furthermore, the appearance of an opposite biphasic trend in the means of the serum ratios is significant on the repeated measures MANOVA, $F(3,31)=3.38$, $p=0.0306$.

There also are significant compartment-specific variations in the apparent activity of ISOT. The results of the repeated measures MANOVA indicate that all three of the dependent measures (HAL, OH-HAL, and the ratio OH-HAL/HAL) are affected differently across the three different tissue compartments. The data are consistent with other evidence with the activities of retinoids such as ISOT are tissue specific (Chytil, F.;

Retinoic acid; biochemistry, pharmacology, toxicology, and therapeutic use. Pharmacol. Rev., 1984,36,93s-100s).

EXAMPLE 9

To demonstrate the neuroleptic activity of the retinoic acids in mammals, their tranquilizing effect in mice was tested in the following manner. Female albino laboratory mice from the National Institute of Health stock weighing between 20 to 30 grams were maintained in home cages in groups of less than ten. They were injected intraperitoneally with a suspension of retinoic acid in 10% Tween 80 in physiologic saline and returned to their home cage for two hours. They were then placed individually in an unfamiliar plexiglass chamber where their gross motor activity was automatically counted by two grids of photocells: one for horizontal and one for vertical (rearing) activity. The total count accumulated over 30 minutes in a given orientation (horizontal or vertical) is a measure in arbitrary units of the gross motor exploratory activity of the mouse in this novel environment. Because baseline activity varies from day to day, control values are given for each trial. The results for the intraperitoneal injections are given in Table 3.

TABLE 3

| MOUSE ACTIVITY HABITUATION 2 HOURS AFTER 40 MG/KG RETINOIC ACID INTRAPERITONEALLY | | | | |
|---|---|---|---|---|
| ISOMER | HORIZONTAL COUNTS | VERTICAL COUNTS | NUMBER | PROB. (MANOVA) |
| TRETINOIN | 72 ± 36 | 181 ± 81 | 8 | $p < .02$ |
| CONTROL | 128 ± 48 | 453 ± 244 | 8 | |
| ISOTRETINOIN | 117 ± 56 | 371 ± 216 | 4 | $p < .05$ |
| CONTROL | 194 ± 24 | 683 ± 97 | 4 | |

It can be seen from this data that both isomers of retinoic acid cause a similar decrease in spontaneous and exploratory gross motor activity by about 40% in both the vertical and horizontal axis. This is consistent with the fact that there has been demonstrated a naturally occurring enzyme that interconverts these two forms of retinoic acid, and that their activities may be adequately described in some systems as interchangeable.

I claim:

1. A method for treating a patient having a psychotic illness, comprising administering to the patient a combination of haloperidol and a retinoid in a combined amount effective for treating the psychotic illness.

2. The method of claim 1, wherein the psychotic illness is schizophrenia.

3. The method of claim 2, wherein the retinoid is retinoic acid.

4. The method of claim 3, wherein the retinoic acid is isotretinoin or tretinoin.

5. The method of claim 3, wherein the retinoic acid is isotretinoin.

6. The method of claim 5, wherein isotretinoin is administered orally in a pharmaceutical unit dosage form, each unit dosage form containing from about 5 mg to about 40 mg of isotretinoin.

7. The method of claim 6, wherein the pharmaceutical unit dosage form is a tablet or gelatin capsule.

8. The method of claim 7, wherein isotretinoin is administered to the patient in two divided daily doses.

9. The method of claim 5, wherein isotretinoin is administered in a daily dose in the range of about 0.01 mg/kg to about 3 mg/kg of the patient's body weight.

10. The method of claim 5, wherein isotretinoin is administered to the patient in a daily dose in the range of about 0.05 to about 1 mg/kg of the patient's body weight.

11. The method of claim 10, wherein the retinoid is administered to the patient in a daily dose of about 0.5 mg/kg of the patient's body weight.

12. A method for inhibiting the occurrence of movement disorder side effects of a haloperidol in a patient receiving the haloperidol, which method comprises administering a retinoid to the patient in a pharmaceutically effective amount for inhibiting the occurrence of the movement disorder side effects.

13. The method of claim 12, wherein the retinoid is retinoic acid.

14. The method of claim 13, wherein the retinoic acid is tretinoin or isotretinoin.

15. The method of claim 13, wherein the retinoic acid is isotretinoin.

16. A method for treating a patient having a psychotic illness, comprising: administering to the patient in a daily dose a combination of a haloperidol in a range of up to about 0.8 mg/kg of the patient's body weight and a retinoid in a range of about 0.01 mg/kg to about 3 mg/kg of the patient's body weight.

17. The method of claim 16 wherein the haloperidol is administered to the patient in a daily dose of about 0.4 mg/kg of the patient's body weight and the retinoid is administered to the patient in a daily dose of about 0.05 mg to about 1 mg per kg of the patient's body weight.

* * * * *